(12) United States Patent
Zander

(10) Patent No.: US 9,482,673 B2
(45) Date of Patent: *Nov. 1, 2016

(54) METHOD FOR SIMULTANEOUSLY DETERMINING MULTIPLE COAGULATION PROTEASES

(71) Applicant: SIEMENS HEALTHCARE DIAGNOSTICS PRODUCTS GMBH, Marburg (DE)

(72) Inventor: Norbert Zander, Marburg (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/589,425

(22) Filed: Jan. 5, 2015

(65) Prior Publication Data

US 2015/0111785 A1    Apr. 23, 2015

Related U.S. Application Data

(63) Continuation of application No. 13/327,092, filed on Dec. 15, 2011, now Pat. No. 8,932,826.

(51) Int. Cl.

| | |
|---|---|
| *C12Q 1/56* | (2006.01) |
| *C12Q 1/37* | (2006.01) |
| *C12N 9/50* | (2006.01) |
| *G01N 33/573* | (2006.01) |

(52) U.S. Cl.
CPC ............ *G01N 33/573* (2013.01); *C12Q 1/37* (2013.01); *C12Q 1/56* (2013.01); *C12N 9/50* (2013.01); *G01N 2333/96444* (2013.01); *G01N 2333/974* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 4,440,678 A | 4/1984 | Svendsen | 530/331 |
| 4,508,644 A | 4/1985 | Heber et al. | 530/331 |
| 4,598,043 A | 7/1986 | Svendsen | 435/13 |
| 5,334,506 A | 8/1994 | Stuber et al. | 435/23 |
| 5,478,810 A | 12/1995 | Stuber et al. | 514/13.6 |
| 5,510,243 A | 4/1996 | Boyd et al. | 435/18 |
| 8,133,696 B2 | 3/2012 | Giesen et al. | 435/13 |
| 8,802,386 B2 | 8/2014 | Giesen et al. | 435/13 |
| 8,932,826 B2 | 1/2015 | Zander | 435/13 |
| 2006/0024745 A1 | 2/2006 | Pritchard | 435/7.1 |
| 2006/0051828 A1 | 3/2006 | Giesen et al. | 435/13 |
| 2011/0306058 A1 | 12/2011 | Van Dreden et al. | 435/7.4 |

FOREIGN PATENT DOCUMENTS

| | | | |
|---|---|---|---|
| CN | 1650170 A | 8/2005 | C12Q 1/56 |
| CN | 1729399 A | 2/2006 | C07K 16/40 |
| CN | 101512011 A | 8/2009 | C12Q 1/56 |
| CN | 101605907 A | 12/2009 | C12Q 1/56 |
| EP | 0034122 B1 | 8/1981 | C07K 14/00 |
| EP | 0078764 A1 | 5/1983 | C07K 5/083 |
| EP | 0258784 A2 | 3/1988 | C07K 1/02 |
| EP | 0456152 A2 | 11/1991 | A61K 38/00 |
| EP | 1833982 B1 | 12/2010 | C12Q 1/56 |
| WO | 2004/041840 A2 | 5/2004 | C07K 1/13 |
| WO | 2006/072602 | 7/2006 | C12Q 1/56 |
| WO | 2007/141023 A2 | 12/2007 | C12Q 1/56 |

OTHER PUBLICATIONS

Van Wijk, Eduard M. et al., "Mechanized Amidolytic Technique for Determination of Factor X and Factor-X Antigen, and its Application for Patients Being Treated with Oral Anticoagulants," Clinical Chemistry, 26(7):885-890, 6 pages, 1980.

Kojima, Hirotatsu et al., "Fluorescent Indicators for Nitric Oxide Based on Rhodamine Chromophore," Tetrahedron Letters, vol. 41, No. 1, Elsevier, 4 pages, 2000.

Nguyen, Kiet T. et al., "Slow-Binding Inhibition of Peptide Deformylase by Cyclic Peptidomimetrics as Revealed by a New Spectrophotometric Assay," Bioorganic Chemistry, vol. 32, No. 3, 14 pages, Jun. 1, 2004.

Bates, Shannon M. et al., "Coagulation Assays," Circulation, 112:e53-e60, 9 pages, 2005.

Rosén, S., "Chromogenetic Methods in Coagulation Diagnostics," Hamostaseologie, 25:259-266, 8 pages, 2005.

European Search Report, Application No. 1015869, 6 pages, Apr. 15, 2011.

*Primary Examiner* — Jennifer Pitrak McDonald
*Assistant Examiner* — Qing Xu
(74) *Attorney, Agent, or Firm* — Slayden Grubert Beard PLLC

(57) ABSTRACT

The present invention relates to a chromogenic method for simultaneously determining the activity of multiple coagulation proteases or for simultaneously determining the inhibition of multiple coagulation proteases in a single test reaction. For this purpose, use is made of two chromogenic substrates which have different absorption maxima and whose color signals can be separated spectrally.

5 Claims, 1 Drawing Sheet

METHOD FOR SIMULTANEOUSLY DETERMINING MULTIPLE COAGULATION PROTEASES

CROSS-REFERENCE TO RELATED APPLICATIONS

This application is a continuation of U.S. application Ser. No. 13/327,092 filed on Dec. 15, 2011, which is incorporated herein in its entirety.

The present invention is in the field of coagulation diagnostics and relates to a method for simultaneously determining the activity of multiple coagulation proteases or for simultaneously determining the inhibition of multiple coagulation proteases.

Established anticoagulant therapies aim primarily to inhibit the procoagulatory coagulation factors thrombin (factor Imia) and factor Xa. A distinction is made between oral anticoagulation with vitamin K antagonists, such as Coumadin for example, resulting in inhibition of coagulation factor synthesis, and anticoagulation by inhibition of active coagulation factors in the bloodstream. In the case of the Anticoagulants which inhibit or inactivate active coagulation Factors in the bloodstream, a distinction is made between Anticoagulants having a direct effect and those having an Indirect effect. Anticoagulants having a direct effect, such as Rivaroxaban, dabigatran or melagatran for example, bind to Thrombin or factor Ax and are therefore highly specific. Anticoagulants having an indirect effect, such as heparins for Example, bind to endogenous coagulation factor inhibitors, such As ant thrombin for example, and intensify the anticoagulatory Effect thereof many times over.

All anticoagulants which inhibit active coagulation factors in The bloodstream are characterized by a specific inactivation Pattern. Certain substance classes, such as unfractionated, high-molecular-weight heparins for example, inhibit both thrombin and factor Xa. Other substances have a highly specific effect, i.e., inhibit either thrombin (e.g., hirudin, dabigatran, melagatran) or factor Xa (e.g., pentasaccharides such as fondaparinux, rivaroxaban).

During the course of treatment of a thromboembolic disease, the anticoagulant is sometimes changed. A classic case is the transition from heparin (inhibition of thrombin and factor Xa in the bloodstream) to Coumadin (inhibition of coagulation factor synthesis in the liver) when treating deep vein thromboses in legs. With such changes in therapy, the relative inactivation of thrombin and factor Xa in the bloodstream can change. For the control of the therapy and the dosing of the medicaments, it is important to know the activity or the inhibition of thrombin and of factor Xa. Therefore, it is necessary to be able to reliably determine the activity or the inhibition of the active coagulation factors thrombin and factor Xa in the blood of a patient.

In coagulation diagnostics, a distinction is made between "global tests" for examining the functionality of the blood coagulation cascade and "individual tests" for determining the activity of individual blood coagulation factors. Different test formats are known both for the global tests and for the individual tests. With regard to the test format, a distinction is essentially made between coagulation tests and chromomeric tests.

In a chromomeric test, the patient sample to be examined, which usually consists of plasma, is mixed with a coagulation activator and with a substrate for a coagulation factor. Since most blood coagulation factors are serine end peptidases, i.e., hydrolyses which can cleave peptide bonds, use is mainly made of peptide substrates which are cleaved highly specifically by the blood coagulation factor to be determined and which have a detectable signal group. Preferably, use is made of cleavable chromomeric or fluorogenic signal groups, which are determined photo metrically. Patent documents EP 0034122 A1 and U.S. Pat. No. 4,508,644 describe a multitude of chromomeric peptide substrates and their use in coagulation diagnostic tests, for example for determining the proteolysis coagulation factors factor Imia (thrombin) and Xa. Document EP 0078764 A1 describes a chromomeric method for determining the proteolysis coagulation factor Ixia.

Chromomeric tests in particular can also be used to determine anticoagulants, which inhibit the activity of blood coagulation factors, in patient samples. For this purpose, the patient sample to be examined is usually mixed with an activated coagulation factor and with a substrate for said coagulation factor. The more anticoagulant present in the sample, the greater the inhibition of the activated coagulation factor and the less substrate cleaved.

Established chromomeric tests, which are also commercially available, use in particular the chromospheres para-nitroaniline (pNA) and 5-amino-2-nitro benzoic acid (ANBA), which have an absorption maximum at 405 nm. The resulting yellow color is generally determined photo metrically. When determining anticoagulants, the color concentration in the test reaction is inversely proportional to the anticoagulant concentration in the sample.

To determine the inhibition of thrombin and factor Xa, it is necessary to carry out two separate tests in which the inhibition of one of the two coagulation factors is determined in each case. It would be desirable to simultaneously determine the activity or inhibition of the two coagulation factors in a single test reaction. This would have the advantages of reducing material consumption and time expenditure and of carrying out both determinations under the same conditions, avoiding variations while carrying out the tests, such as pupating errors for example, which might lead to an error in determining the relation between the two results.

The object of the present invention is, therefore, to provide a method which allows the simultaneous determination of thrombin and factor Xa in a single test reaction. WO 2006/072602 A1describes a method for simultaneously determining thrombin and plasmid, an enzyme of the fibrinolytic system, wherein fluorescent substrates are used.

The object underlying the invention is achieved by mixing a sample with a first chromomeric substrate specific for the first proteolysis coagulation factor and with a second chromomeric substrate specific for the second proteolysis coagulation factor, wherein the first chromomeric substrate has a chromospheres whose absorption maximum differs by at least 100 nm from the absorption maximum of the chromospheres of the second chromomeric substrate. The resulting chromomeric signals can be separated spectrally and can be determined photo metrically, independently of one another, at different wavelengths.

The present invention thus provides a method for simultaneously determining the activity of a first proteolysis coagulation factor and of a second proteolysis coagulation factor in a single test reaction, wherein a sample is mixed with a first chromomeric substrate specific for the first proteolysis coagulation factor and with a second chromomeric substrate specific for the second proteolysis coagulation factor, and wherein the absorption change in the test reaction (color signal formation) is determined photo metrically, and wherein the first chromomeric substrate has a chromospheres whose absorption maximum differs by at least 100 nm from the absorption maximum of the chromospheres of the second chromomeric substrate.

The term "proteolysis coagulation factor" is to be understood to mean any plasma serine protease which has a procoagulatory (coagulation-promoting), anticoagulatory (coagulation-inhibiting) or fibrinolytic (clot-degrading) function in a mammalian, preferably human, blood coagulation system. Procoagulatory proteolysis coagulation factors are, for example, factor Imia (thrombin), factor Via, factor Ixia, factor Xa, factor Xiao, and factor Ixia. An anticoagulatory proteolysis coagulation factor is, for example, protein Ca (activated protein C). A fibrinolytic proteolysis coagulation factor is, for example, plasmid.

The term "simultaneous determination" is to be understood to mean the determination of the two proteolysis coagulation factors in a single test reaction.

In the context of the invention, a "sample" is to be understood to mean the material which is suspected of containing the proteolysis coagulation factors to be detected or the anticoagulant(s) to be determined. The term "sample" comprises in particular human or animal body fluids, especially blood and plasma.

A "chromomeric substrate specific for a proteolysis coagulation factor" is to be understood to mean a substrate which is converted with sufficient specificity by a proteolysis coagulation factor, wherein a chromospheres is released as a result of the specific substrate conversion. Cleavable substrates, in particular, which have at least one cleavage site for an activated coagulation factor, are sufficiently known to a person skilled in the art. A cleavable substrate can be a molecule which is broken down into two cleavage products by the action of the activated proteolysis coagulation factor, which molecule is a molecule which has been prepared synthetically, recombinant or using biotechnological methods or is a natural molecule. A cleavable substrate can entirely or partly consist of a peptide. Preferably, it comprises a peptide portion at least in the region of the cleavage site. Preferably, the peptide portion of a cleavable substrate consists of 3 to about 150 amino acid residues. Patent documents EP 0034122 A1 and U.S. Pat. No. 4,508,644 describe a multitude of chromomeric peptide substrates, their preparation, and their use in coagulation diagnostic tests, for example for determining the coagulation factors factor Imia (thrombin) and Xa. Document EP 78764 A1 describes a chromomeric method for determining the coagulation factor Ixia.

A "chromophore" is to be understood to mean a signal group ("label") which can be cleaved (dissociated) from the substrate by the action of a specific proteolysis coagulation factor and which, after cleavage of the substrate, has absorption properties different from those in the nucleated state. According to the invention, the first chromomeric substrate has a chromospheres whose absorption maximum, after cleavage, differs by at least 100 nm from the absorption maximum of the chromospheres of the second chromomeric substrate after cleavage. Table 1 shows a selection of known chromospheres, their absorption maxima after cleavage, and preferred combinations of chromospheres whose absorption maxima differ by at least 100 nm from one another. Preferred chromospheres are those which, after cleavage from the substrate, have an absorption maximum in the visible wavelength range from 380 nm to 780 nm.

The activity of the coagulation factors is determined by photometric determination of absorption change (color signal formation) in the test reaction, which change is proportional to the activity of the coagulation factors. The term "photometric determination of absorption change" are to be understood to mean an absorption measurement in which the reduction in intensity of a light beam transmitted through the test reaction is measured (transmission measurement). In order to measure the color signal formation, a wavelength region is selected which is absorbed by the dissociated chromospheres to be determined.

According to the invention, photometric determination of absorption change comprises absorption measurement of the test reaction at at least two different wavelengths, which preferably lie in the region of the absorption maxima of the chromophores used. Alternatively, the test reaction can be illuminated with white light, which is broken down spectrally after passage through the test reaction. Measurement of the absorption change of the test reaction over time can be achieved by means of alternating pulses of light of wavelengths corresponding to the absorption maxima of the two chromophores used, the pulses alternating at short intervals.

TABLE 1

| Chromophore | Absorption maximum | Combinable with |
|---|---|---|
| para-Nitroaniline (pNA) | 405 nm | Color Index Basic Blue 49 or 124 |
| 5-Amino-2-nitrobenzoic acid (ANBA) | 405 nm | Color Index Basic Blue 49 or 124 |
| Color Index Basic Blue 49 | 625 nm | pNA, ANBA |
| Color Index Basic Blue 124 | 625 nm | pNA, ANBA |

Particularly preferred chromophores are phenoxazime derivatives, such as, for example, Color Index Basic Blue 49 (C.I. Basic Blue 49, CAS registration number 11075-19-7) or Color Index Basic Blue 124 (C.I. Basic Blue 124, CAS registration number 89106-91-2), which have an absorption maximum of about 600 nm and bring about blue coloration. Patent document EP 0258784 A2 discloses particularly preferred phenoxazime derivatives and correspondingly labeled peptide substrates.

The method according to the invention can be used for simultaneously determining the activity of two proteolysis coagulation factors which are present in the sample of a patient in order to examine the coagulation status of a patient. For this purpose, the sample is usually mixed, before the addition of the two chromomeric substrates, with one or more agents which bring about direct or indirect activation of the proteolysis coagulation factors to be determined. Direct activation is to be understood to mean that an agent is used which directly activates the proteolysis coagulation factor to be determined, independently of the presence of other coagulation factors. Indirect activation is to be understood to mean that an agent is used which activates one or more blood coagulation factors of the blood coagulation cascade, which in turn activate the proteolysis coagulation factor to be examined. The type of agent depends on which coagulation factor is to be determined, whether the activity of the coagulation factor is to be determined on its own, or whether the functionality of the blood coagulation cascade or of a section of the blood coagulation cascade (extrinsic or intrinsic pathway) is to be determined on the basis of a coagulation factor. Substances and specific mixtures of various substances which enable direct or indirect activation of proteolysis coagulation factors are sufficiently known to a person skilled in the art and comprise, for example, phospholipids, such as negatively charged phospholipids for example; lipoproteins, such as thromboplastin for example; proteins, such as tissue factor for example, activated serine proteases, such as, for example, factor Imia (thrombin), factor Via, factor Ixia, factor Xa, factor Xiao, factor Ixia, or activated protein C; snake poisons, such as, for example, PROTAC® enzyme, cairn, texturing, onscreen, batroxobin, thrombolytic, or Russell's viper venom (RVV); contact activators, such as, for example, silica, kaolin, pelagic acid, or Elite. Further substances which may contain an activating agent is, for example, buffer substances, salts, detergents, ions, in particular calcium ions, and chelating agents.

In one embodiment, an inhibitor of fibrin aggregation can be additionally added to the test reaction. A fibrin aggregation inhibitor is to be understood to mean a substance, in particular a synthetic oligopeptide, which inhibits the association (polymerization) of fibrin monomers formed by the action of thrombin and thus prevents clot formation in the reaction mixture, which might impair photometric determination of color signals (see, for example, EP 0456152 B1).

Furthermore, the method according to the invention can be used for simultaneously determining the activity of two proteolysis coagulation factors which have been added to the sample of a patient in order to examine the anticoagulatory potential of a patient. For this purpose, the patient sample is mixed with defined amounts of at least two procoagulatory proteolysis coagulation factors and with the two chromomeric substrates specific for the coagulation factors added, and the inhibition of the proteolysis activity of the coagulation factors is determined. The greater the anticoagulatory potential of the patient, i.e., the more anticoagulant present in the sample, the greater the inhibition of the activated procoagulatory coagulation factor(s) and the less substrate cleaved. The inhibition of the proteolysis activity of the coagulation factors can be quantified by comparison with a control test reaction in which a normal sample containing no anticoagulant, for example normal human plasma, is used as a sample.

Which activated coagulation factors are added depends on which anticoagulants are to be determined.

For the determination of a heparin, i.e., a high-molecular-weight, unfractionated heparin (HMW heparin) or a low-molecular-weight heparin (LMW heparin) or a heparin, it is particularly useful to add factor Imia (thrombin) or factor Xa. For the determination of a direct thrombin inhibitor, for example agrarian, melagatran, ximelagatran, bivalirudin, dabigatran or hirudin, it is particularly useful to add factor Imia (thrombin). For the determination of a direct factor Xa inhibitor, for example rivaroxaban, it is particularly useful to add factor Xa.

The present invention further relates to a test kit for determining the anticoagulatory potential of a patient sample. A test kit according to the invention comprises a first reagent having a defined concentration of a first proteolysis coagulation factor, and a second reagent having a defined concentration of a second proteolysis coagulation factor, and
 a) a third reagent containing a first chromomeric substrate specific for the first proteolysis coagulation factor and a second chromomeric substrate specific for the second proteolysis coagulation factor; or
 b) a third reagent containing a first chromomeric substrate specific for the first proteolysis coagulation factor and a fourth reagent containing a second chromomeric substrate specific for the second proteolysis coagulation factor,
wherein the first chromomeric substrate has a chromospheres whose absorption maximum differs by at least 100 nm from the absorption maximum of the chromospheres of the second chromomeric substrate.

In a preferred test kit, the first chromomeric substrate specific for the first proteolysis coagulation factor has a chromospheres from the group comprising para-nitroaniline and 5-amino-2-nitro benzoic acid, and the second chromomeric substrate specific for the second proteolysis coagulation factor has a chromospheres from the group comprising phenoxazime derivatives, or vice versa.

A particularly preferred test kit comprises a first reagent having a defined thrombin concentration and a second reagent having a defined factor Xa concentration and at least one further reagent containing a thrombin-specific and/or a factor Xa-specific chromomeric substrate, wherein the thrombin-specific chromomeric substrate has a chromospheres whose absorption maximum differs by at least 100 nm from the absorption maximum of the chromospheres of the factor Xa-specific chromomeric substrate. The two substrates may be present in a single reagent or in separate reagents. Preferably, the thrombin-specific chromomeric substrate has a chromospheres from the group comprising para-nitroaniline and 5-amino-2-nitro benzoic acid, and the factor Xa-specific chromomeric substrate has a chromospheres from the group comprising phenoxazime derivatives, or vice versa.

The reagents of the test kit according to the invention may be provided in liquid or lyophilized form. In the event that some or all reagents of the test kit are present as lyophilisates, the test kit may additionally contain the solvents required for dissolving the lyophilisates, such as, for example, distilled water or suitable buffers.

Figure 1:
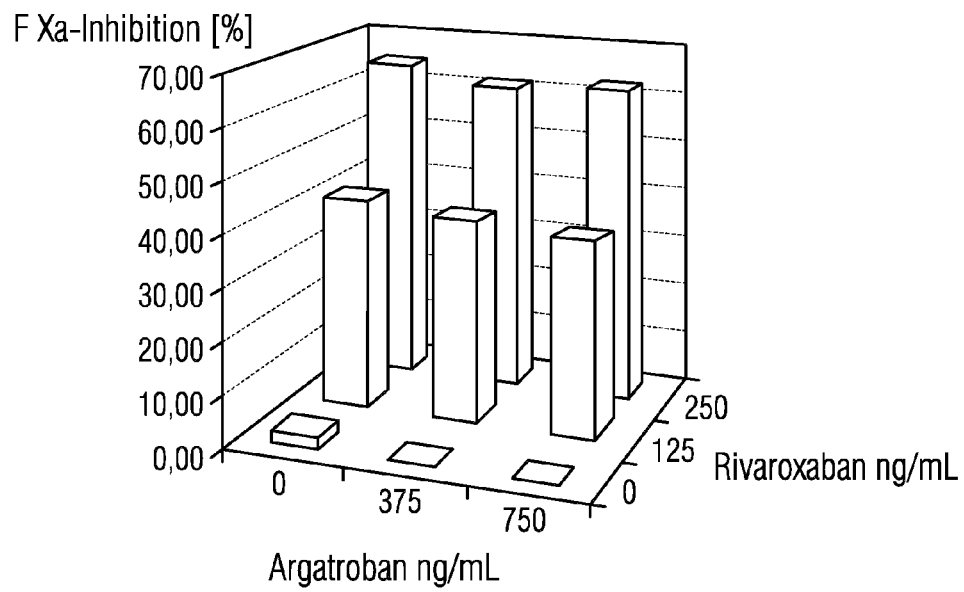
FIG. 1 Bar chart showing the inhibition of factor Xa activity [%] in normal plasma samples enriched with rivaroxaban and/or agrarian at various concentrations (see example 2). Cleavage of the factor Xa-specific peptide substrate having an ANBA chromospheres were measured at a wavelength of 405 nm. Irrespective of the agrarian concentration (thrombin inhibitor), increased factor Xa inhibition is measured in samples having an increased rivaroxaban concentration (factor Xa inhibitor).
Figure 2:
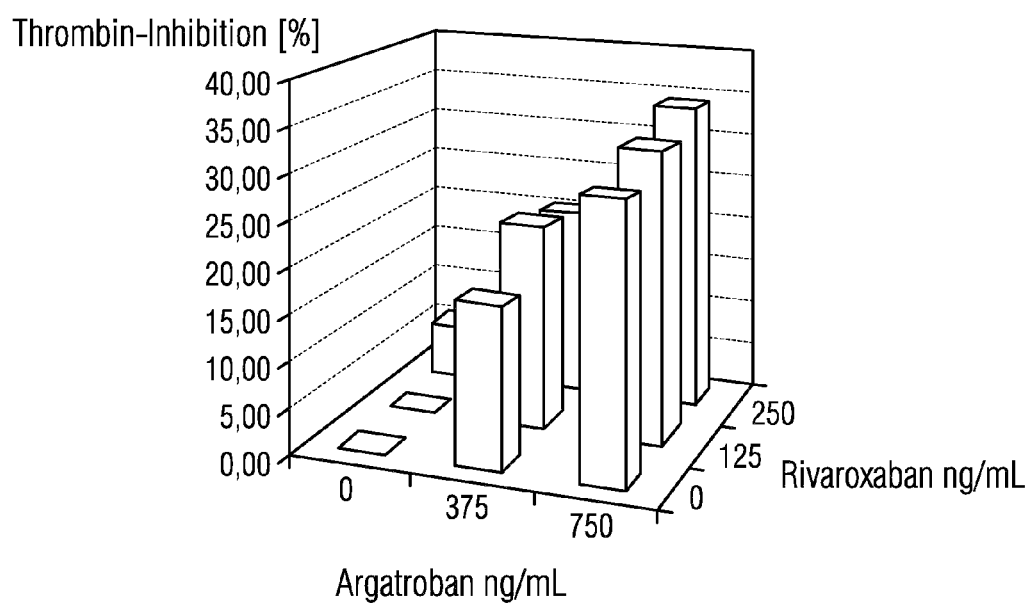
FIG. 2 Bar chart showing the inhibition of thrombin activity [%] in normal plasma samples enriched with rivaroxaban and/or agrarian at various concentrations (see example 2). Cleavage of the thrombin-specific peptide substrate having a Basic Blue 49 chromospheres was measured at a wavelength of 575 nm. Irrespective of the rivaroxaban concentration (factor Xa inhibitor), increased thrombin inhibition is measured in samples having an increased agrarian concentration (thrombin inhibitor).

The following exemplary embodiments serve to illustrate the method according to the invention and are not to be understood as limiting.

EXAMPLES

Example 1

Simultaneous Determination of Thrombin Activity and of Factor Xa Activity in Blood Plasma in a Single Reaction The following components were mixed to form one reaction:

| | |
|---|---|
| 10 μl | sample |
| 10 μl | pool of normal human plasma |
| 40 μl | substrate reagent (4 mM Z-D-Leu-Gly-Arg-ANBA-methylamide, 0.8 mM Tos-Gly-Pro-Arg-Basic Blue 49 in mannitol buffer, pH 4.0) |
| 100 μl | factor Xa reagent (0.75 U/ml human factor Xa in 4.5 g/l TRIS, 9 g/l NaCl, 0.56 g/l EDTA, pH 8.0) |
| 100 μl | thrombin reagent (5 U/ml bovine thrombin in 1.2 g/l TRIS, pH 8.2) |

The sample used was normal human plasma. Factor Xa cleaves ANBA from the factor Xa-specific peptide substrate Z-D-Leu-Gly-Arg-ANBA-methylamide, increasing over time the optical density in the reaction at a wavelength of 405 nm. At the same time, thrombin cleaves Basic Blue 49 from the thrombin-specific peptide substrate Tos-Gly-Pro-Arg-Basic Blue 49, increasing over time the optical density in the reaction at a wavelength of 575 nm.

The measurements of the optical densities of the reaction at 405 nm and 575 nm and the evaluation of the reaction kinetics were carried out simultaneously in a fully automated Sysmex® CS-2000I coagulation analyzer. To measure the optical densities, the reaction was irradiated alternately with light of the aforementioned wavelengths, and the absorbance of the light, caused by the coloration of the reaction, was determined as a function of wavelength and time.

The increases in the reaction kinetics correlate with the respective enzyme activity. For a normal plasma sample, the factor Xa-specific absorbance change at 405 nm was 0.236 per minute, whereas the thrombin-specific absorbance change at 575 nm was 0.111 per minute.

Example 2

Simultaneous Determination of Thrombin and Factor Xa Inhibitors in a Single Reaction Normal plasma was enriched with various concentrations of rivaroxaban, a specific factor Xa inhibitor, and/or of agrarian, a specific thrombin inhibitor, and used as a sample in a method as per example 1.

The increases in the reaction kinetics for normal plasma without inhibitors were defined as 100% of the respective enzyme activity. The results of the plasma samples having various inhibitor concentrations were evaluated on the basis of this reference. The results (inhibition in %) are summarized in table 2.

TABLE 2

| Rivaroxaban (ng/ml) | Argatroban (ng/ml) | F Xa inhibition [%] | Thrombin inhibition [%] |
|---|---|---|---|
| 0 | 0 | 2 | 0 |
| 0 | 375 | 0 | 18 |
| 0 | 750 | 0 | 31 |
| 125 | 0 | 42 | 0 |
| 125 | 375 | 40 | 23 |
| 125 | 750 | 39 | 33 |
| 250 | 0 | 65 | 5 |
| 250 | 375 | 62 | 22 |
| 250 | 750 | 63 | 35 |

The results show that the use of two chromomeric substrates having different enzyme specificities and having chromophores which have different absorption maxima allow the simultaneous, independent determination of inhibitors specific for different coagulation factors in a single reaction.

The invention claimed is:

1. A method for determining anti-thrombin and anti-factor Xa anticoagulant concentrations in a test sample which contains human plasma and which is suspected of containing an anti-thrombin anticoagulant, an anti-factor Xa anticoagulant, or a combination thereof, the method comprising:
   performing a single test reaction by mixing the test sample which contains the human plasma and which is suspected of containing the anti-thrombin anticoagulant, the anti-factor Xa anticoagulant, or the combination thereof, with selected substances including (a) a defined amount of thrombin, (b) a defined amount of factor Xa, (c) a first chromogenic substrate specific for thrombin, and (d) a second chromogenic substrate specific for factor Xa, wherein a chromophore of the first chromogenic substrate and a chromophore of the second chromogenic substrate have respective absorption maximums that differ by at least 100 nm;
   photometrically determining absorption changes in the single test reaction over time;
   comparing the photometrically determined absorption changes in the single test reaction with photometrically determined absorption changes occurring in a control test reaction between an anticoagulant-free control sample and the selected substances;
   determining inhibition of the absorption changes caused by the anti-thrombin and/or anti-factor Xa anticoagulants in the test sample based on the comparison of the photometrically determined absorption changes; and
   determining the anti-thrombin and anti-factor Xa anticoagulant concentrations in the test sample based on the inhibition of the absorption changes in the single test reaction.

2. The method of claim 1, wherein the chromophore of the first chromogenic substrate or the chromophore of the second chromogenic substrate comprises para-nitroaniline or 5-amino-2-nitrobenzoic acid.

3. The method of claim 1, wherein the chromophore of the first chromogenic substrate or the chromophore of the second chromogenic substrate comprises a phenoxazine derivative.

4. The method of claim 1, wherein:
   the chromophore of the first chromogenic substrate comprises para-nitroaniline or 5-amino-2-nitrobenzoic acid; and
   the chromophore of the second chromogenic substrate comprises a phenoxazine derivative.

5. The method of claim 1, wherein:
   the chromophore of the first chromogenic substrate comprises a phenoxazine derivative; and
   the chromophore of the second chromogenic substrate comprises para-nitroaniline or 5-amino-2-nitrobenzoic acid.

* * * * *